United States Patent
Shin et al.

(10) Patent No.: US 12,042,545 B2
(45) Date of Patent: Jul. 23, 2024

(54) ENCAPSULATED EXTRACELLULAR VESICLES

(71) Applicant: THE BOARD OF TRUSTEES OF THE UNIVERSITY OF ILLINOIS, Urbana, IL (US)

(72) Inventors: Jae-Won Shin, Chicago, IL (US); Stephen Lenzini, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 196 days.

(21) Appl. No.: 17/500,423

(22) Filed: Oct. 13, 2021

(65) Prior Publication Data
US 2022/0111068 A1   Apr. 14, 2022

Related U.S. Application Data

(60) Provisional application No. 63/091,534, filed on Oct. 14, 2020.

(51) Int. Cl.
*A61K 47/69* (2017.01)
*C12N 1/20* (2006.01)

(52) U.S. Cl.
CPC ............ *A61K 47/6903* (2017.08); *C12N 1/20* (2013.01)

(58) Field of Classification Search
CPC .. A61K 47/6903; C12N 1/20; C12N 2533/90; C12N 5/0012; C12N 5/0663; C12N 5/069; C07K 14/705
See application file for complete search history.

(56) References Cited

U.S. PATENT DOCUMENTS

2017/0196818 A1* 7/2017 Shin ................ A61K 35/12

FOREIGN PATENT DOCUMENTS

| WO | 2014168548 A2 | 10/2014 | |
|---|---|---|---|
| WO | 2017087500 A1 | 5/2017 | |
| WO | 2017117585 A1 | 7/2017 | |
| WO | 2020196986 A1 | 1/2020 | |
| WO | WO-2020047071 A1 * | 3/2020 | ......... A61K 31/7105 |
| WO | 2020261257 A1 | 12/2020 | |

OTHER PUBLICATIONS

Fuhrmann, G. Diffusion and transport of extracellular vesicles, Nature Nanotechnology, Jan. 27, 2020 (Year: 2020).*
Oshikawa et al., "Aquaporins in Urinary Extracellular Vesicles (Exosomes)", Int. J. Mol. Sci., Jul. 2016, 17(16):957. 9 pages.*
Wen et al., "Urinary Excretion o fAquaporin-2 in Rat Is Mediated by a Vasopressin-Dependent Apical Pathway", J. Am. Soc. Nephol., 1999, 10:1416-1429.*

* cited by examiner

*Primary Examiner* — Suzanne M Noakes
(74) *Attorney, Agent, or Firm* — Licata & Tyrrell P.C.

(57) ABSTRACT

Disclosed are recombinant extracellular vesicles (EVs), compositions including modified EVs encapsulated in a matrix, methods for controlling the release of EVs from an encapsulating matrix, and methods of using the same in the treatment of disease.

14 Claims, 2 Drawing Sheets
Specification includes a Sequence Listing.

ENCAPSULATED EXTRACELLULAR VESICLES

This application claims the benefit of priority from U.S. Provisional Application Ser. No. 63/091,534, filed Oct. 14, 2020, the content of which is incorporated herein by reference in its entirety.

This invention was made with government support under grant nos. HL141255, HL125884, and HL007829 awarded by the National Institutes of Health. The government has certain rights in this invention.

BACKGROUND

Extracellular vesicles (EVs) are important mediators of intercellular communication. They are also important biomarkers in the diagnosis of many diseases, such as cancer. As drug delivery vehicles, EVs offer many advantages over traditional drug delivery methods, especially for gene therapy. However, upon administration in animals, EVs can be cleared very rapidly with little accumulation in target tissues. In addition, the extracellular matrix (ECM) that provides structure to tissues is generally very dense and acts as a barrier to EV penetration. This represents a hurdle to translation of EV therapies because administration of EVs does not necessarily lead to their penetration into denser tissues.

WO 2020/196986 A1 suggests methods for controlling angiogenesis-related cytokines of stem cell-derived EVs using the mechanical strength of a gelatin methacryloyl hydrogel. WO 2017/087500 A1 suggests delivery of EVs in a biocompatible scaffold, such as a hydrogel and WO 2020/261257 A1 describes a method for producing EVs from stem cells by providing shear stress stimulation to a population of stem cells in a three-dimensional porous scaffold so that EVs are secreted into the medium and can be collected. However, these references do not address the properties of the hydrogel that modulate release of the EVs upon administration. Accordingly, improved EV compositions and methods to deliver EVs are needed in the art.

SUMMARY OF THE INVENTION

This invention is based on the discovery that water permeation occurs on the surface of EVs through water channels, allowing regulation of internal water content, leading to deformation and the ability to transport through denser matrix materials. Thus, matrix materials (e.g., hydrogels and ECM) possessing a range of mechanical properties and/or EVs harboring a modified number of water channels on their surface solve the problem of low EV accumulation in tissues.

Accordingly, one aspect of this invention relates to a recombinant EV having a modified number of one or more water channel proteins compared to a wild-type EV. In some embodiments, the recombinant EV is isolated from a recombinant producer cell harboring a nucleic acid construct encoding the one or more water channel proteins.

In another aspect, the invention provides a composition including EVs encapsulated in a matrix, wherein the EVs have a modified number of one or more water channel proteins compared to a wild-type EVs. In one embodiment, the EVs are isolated from a recombinant producer cell harboring a nucleic acid construct encoding the one or more water channel proteins. In other embodiments, the matrix is a hydrogel or artificial extracellular matrix, wherein said hydrogel has a complex modulus G* in the range of 0.3 kPa to 3 kPa and/or exhibits a stress relaxation rate between 10 seconds and 100 seconds. A method for using the composition to treat a subject in need thereof is also provided, wherein in some embodiments said subject is suffer from a lung injury, e.g., endotoxin-induced acute lung injury, infection-mediated lung injury, or fibrotic lung injury.

In a further aspect, the invention provides a method of controlling release of EVs from an encapsulating matrix by modifying the number or activity of one or more water channel proteins on the surface of said EVs. In one embodiment, the number of one or more water channel proteins is modified by isolating EVs from a recombinant producer cell harboring a nucleic acid construct encoding the one or more water channel proteins. In another embodiment, the activity of the one or more water channel proteins is modified by exposing the EVs to a hypertonic medium or one or more ion channel inhibitors. In a further embodiment, the number of one or more water channel proteins is modified by isolating EVs from a recombinant producer cell harboring a nucleic acid construct encoding one or more siRNAs that inhibit the expression of the one or more water channel proteins.

DETAILED DESCRIPTION OF THE INVENTION

Figure 1:
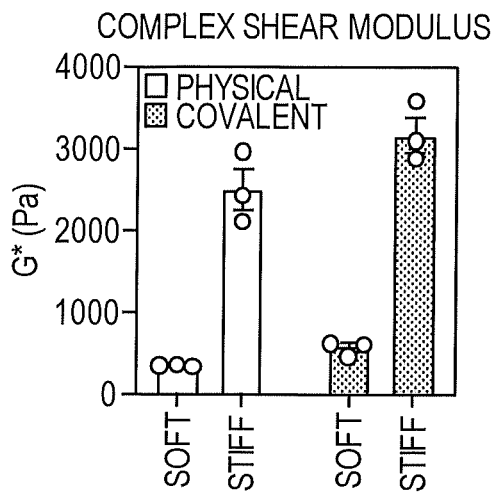
FIG. 1 shows complex shear modulus of the hydrogels calculated at 1 Hz. The data represent the mean of N=3 hydrogels. Error bars are s.e.m.

Cells release extracellular vesicles (EVs) to communicate over long distances, requiring EVs to traverse the extracellular matrix (ECM). However, given that the size of EVs is generally larger than the mesh size of the ECM, it had not been previously known how EVs travel through the dense ECM. It has now been found that EVs readily transport through nanoporous ECM. Using engineered hydrogels, it has been demonstrated that the mechanical properties of the matrix regulate anomalous EV transport under confinement. Matrix stress relaxation allows EVs to overcome confinement, and a higher crosslinking density facilitates fluctuating transport motion through the polymer mesh, leading to free diffusion and fast transport. Furthermore, water permeation through water channel proteins such as aquaporin-1 (AQP1) mediates EV deformability, which further supports EV transport in hydrogels and decellularized matrix. The results presented herein demonstrate the nature of EV transport within confined environments and show an unexpected dependence on matrix mechanics and water permeation. Accordingly, this invention provides for modified EVs and a range of matrix mechanical properties that can be modulated to increase or decrease EV release from an encapsulating matrix. Moreover, modification of water channel protein levels can be extended to other vesicles with lipid bilayers that have a similar difficulty in traversing dense tissues. Examples include, but are not limited to, liposomes, platelets, red blood cells, or therapeutic cells. As such, this invention has broad applicability to therapies that seek to deliver EVs or cells to target tissues and in the treatment of disease.

Accordingly, in some aspects, this invention provides a method for controlling release of EVs from an encapsulating matrix by modifying the number or activity of one or more water channel proteins on the surface of said EVs. As used herein, "extracellular vesicles" or "EVs" refer to membrane-bound structures released from or otherwise derived from cells. EVs include exosomes, microvesicles, apoptotic bodies, ectosomes, and high-density lipoprotein (HDL)-particles surrounded by a double lipid membrane structure and have various types of proteins (enzymes, growth factors, receptors and cytokines), membranous lipids, nucleic acids and metabolites as their main contents. These structures are not limited in any way with regard to in vivo localization (e.g., intracellular or extracellular), in a body fluid, in a cell culture media, generated by in vitro cultured cells, mechanism of origin or size characteristics. An EV can range in size with a lower size limit of at least, about 20 nanometers (nm) in diameter, or alternatively, 30 nm, or 40 nm, or 50 nm in diameter. In some embodiments, an EV has an upper size limit of not more than about 1,000 nm (i.e., 1.0 micrometer, micron, or μm), or alternatively, not more than about 1,500 nm, about 2,000 nm or about 2,500 nm. In this respect, EVs generally have a larger diameter than the average mesh size of the ECM. EVs are suggested to act as nano-shuttles for the transport and delivery of information from one location and/or cell type to distant locations and/or other cell types (Mathivanan & Simpson (2010) *J. Proteomics* 73(10):1907-1920). Also, EVs are theorized to be involved in a wide variety of physiological processes, including cardiac disease, adaptive immune responses to pathogens, and in tumor biology. EVs are thought to play a role in immune system cellular communication, for example, involving dendritic cells and B cells (Raposo, et al. (1996) *J. Exp. Med.* 183:1161). In one embodiment, the EV is an exosome.

EVs of the invention can be obtained by (i) exocytosis from multivesicular bodies to produce exosomes, (ii) budding, fission and shedding of EVs directly from a cytoplasmic membrane, or (iii) membranous blebs caused by programmed cell death leading to the formation of apoptotic bodies. Methods for isolating or otherwise obtaining EVs from cells are described herein and in the art. See, e.g., WO 2020/261257 A1, which describes the use of shear stress stimulations of cells cultured on at least one three-dimensional porous scaffold and isolation of EVs secreted from said cells; WO 2017/117585 A1, which includes culturing cells under hypoxia and low serum conditions and isolating EVs by centrifugation, ultrafiltration, filtration, differential centrifugation and column filtration with a 100 kDa to 300 kDa pore size; or WO 2014/168548 A2, which teaches the use of ultrafiltration and size exclusion liquid chromatography methods for isolating and/or purifying EVs.

EVs suitable for use in this invention can be derived, obtained, or isolated from a variety of producer cells. As used herein the term "producer cell" refers to a cell used for generating an EV, e.g., an exosome. A producer cell can be a cell cultured in vitro, or a cell in vivo. Suitable producer cells include stem cells such as embryonic stem cells (ESCs), induced-pluripotent stem cells, pluripotent stem cells, cord blood stem cells, amniotic fluid stem cells, progenitor cells, precursor cells and/or adult stem cells, e.g., neural stem cells, skin stem cells, epithelial stem cells, skeleton muscle satellite cells, mesenchymal stem cells, adipose-derived stem cells, endothelial stem cells, dental pulp stem cells (DPSCs), hematopoietic stem cells, stromal cells, endothelial precursor cells, or placenta-derived stem cells. More specifically, a producer cell includes a cell known to be effective in generating EVs, e.g., HEK293 cells, Chinese hamster ovary (CHO) cells, and mesenchymal stem or stromal cells (MSCs), BJ human foreskin fibroblast cells, fHDF fibroblast cells, AGE.HN® neuronal precursor cells, CAP® amniocyte cells, adipose mesenchymal stem cells, RPTEC/TERT1 cells. In one such embodiment, EVs are derived from MSCs. Additional embodiments provide for EVs including a biomarker. In some such embodiments the biomarker is a tetraspanin, such as, for example, CD63, CD81, CD82, CD53, and CD37. Other biomarkers include ADAM10, CD44, CD90 and AQP1.

As used herein, the terms "isolate," "isolated," and "isolating" or "purify," "purified," and "purifying" and grammatical variants thereof are used interchangeably and refer to the state of a preparation (e.g., a plurality of known or unknown amount and/or concentration) of desired EVs, e.g., exosomes, that have undergone one or more processes of purification, e.g., a selection or an enrichment of the desired EVs. In some embodiments, isolating or purifying as used herein is the process of removing, partially removing (e.g., a fraction) of the EVs from a sample containing producer cells. In some aspects, an isolated EV composition is enriched as compared to the starting material (e.g., producer cell preparations) from which the composition is obtained. This enrichment can be by at least about 10% to at least about 99% as compared to the starting material. Ideally, isolated EV preparations are substantially free of residual biological products (e.g., contaminants). In particular, the isolated EVs are about 90% to about 100% free of any contaminating biological matter. Residual biological products can include abiotic materials (including chemicals) or unwanted nucleic acids, proteins, lipids, or metabolites. In certain aspects, the isolated EVs are about 90% to about 100% free of any macromolecules, e.g., of any nucleic acids, proteins, lipids, and/or carbohydrates. Substantially free of residual biological products can also mean that the EV composition contains no detectable producer cells and that only EVs are detectable.

In certain embodiments, the EVs of the invention are recombinant. In some embodiments, the recombinant EVs are derived from a population of producer cells which has been genetically modified to express one or more proteins, mitochondrial DNAs, nuclear DNAs, mRNAs, and/or microRNAs. In this respect, recombinant EVs derived from such a population of producer cells can include the modifications of the producer cell. Accordingly, the term "recombinant" refers to an alteration or engineering of an EV, e.g., exosome and/or its producer cell, such that the recombinant EV is different from a naturally-occurring or wild-type EV. In some aspects, a recombinant EV described herein differs in composition of a protein, a lipid, a small molecule, a carbohydrate, etc. compared to the composition of a naturally-occurring or wild-type EV.

In one aspect, the recombinant EVs have been genetically modified to express a biological or therapeutic protein and/or microRNA capable of facilitating regeneration and/or improved function of a target tissue. This includes, for example, knockout or transgenic cell lines. For example, the lumen of an EV is modified in its composition of a protein, a lipid, a small molecule, a carbohydrate, etc. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering.

In another aspect, a recombinant EV has a membrane that differs from a wild-type EV membrane by having a modified number or density of one or more water channel proteins. In one embodiment, the recombinant EV has a reduced number or density of one or more water channel proteins compared to a wild-type EV. Reduced water channel proteins levels or density can be achieved by transient knockdown of one or more water channel genes and associated coding and non-coding transcripts within the population of producer cells, via any number of methods known in the art, such as introduction of dsRNA, siRNA, miR, a vector, plasmid, artificial plasmid, and replicative or non-replicative virus. In another embodiment, the recombinant EV has a higher number or density of one or more water channel proteins compared to a wild-type EV. In accordance with this embodiment, a producer cell is modified to include a nucleic acid construct, e.g., a vector, plasmid or virus, encoding one or more water channel proteins.

Water channels or water channel proteins (WCPs) are transmembrane proteins that have a specific three-dimensional structure with a pore that can be permeated by water molecules. WCPs are large families (over 450 members) that are present in all kingdoms of life. WCPs include three subfamilies: (a) aquaporins (AQPs), which are water specific (or selective water channels); (b) aquaglyceroporins (and glycerol facilitators), which are permeable to water and/or other small molecules; and (c) "superaquaporins" or subcellular AQPs. Several characteristic structural features are common to WCPs. WCPs have a relatively small size: most are less than 300 amino acids in length, usually 250-290. Both the N-terminus and the C-terminus are hydrophilic and located in the cytosol. In the amino acid sequence there are two highly conserved regions called NPA boxes with three amino acid residues (asparagine, proline, alanine: Asn-Pro-Ala) and several surrounding amino acids. The NPA boxes have been called the "signature" of WCPs. WCPs have considerable similar sequences of amino acid residues in the first and the second halves of the polypeptide chain (i.e., there are two tandem sequence repeats). There are six transmembrane domains (TMDs), highly hydrophobic, with α-helix structure and five connecting loops. The a-helices are named from the N-end successively H1, H2, H3, H4, H5, and H6, and the loops are named A, B, C, D, and E. The TMDs and the loops form a core (embedded in the membrane lipid bilayer), to which two "legs" (represented by the cytosolic N- and C-ends) are attached. The NPA boxes are located in the loops B and E, which are rather hydrophobic in nature and have short (half) helices HB and HE. The six TMDs (tilted at about 30° with respect to the membrane normal) form a right-handed bundle enclosing the channel (pore) formed by the NPA motifs and the short tetramer helices HB and HE, bended into the six-helix bundle and connected in the center of the bilayer. This structure is called the aquaporin fold. So the channel (pore) is a narrow tunnel in the center of the molecule, that has at the extracellular and cytoplasmic faces funnel-shaped openings (atria or vestibules). The structural features of WCPs are known in the art and described for human RBC AQP1 (hAQP1; Murata, et al. (2000) *Nature* 407:599-605; Ren, et al. (2001) *Proc. Natl. Acad. Sci. USA* 98:1398-1403), bovine AQP1 (bAQP1; Sui, et al. (2001) *Nature* 414:872-878), *E. coli* AQPZ (Savage, et al. (2003) *PLoS Biol.* 1:E72; Jiang, et al. (2006) *J. Biol. Chem.* 281:454-470), eye-lens specific AQP0 (Gonen, et al. (2004) *Nature* 429:193-197; Harries, et al. (2004) *Proc. Natl. Acad. Sci. USA* 101:14045-14050), archaebacterial AQPM (Lee, et al. (2005) *Proc. Natl. Acad. Sci. USA* 102:18932-18937), AQP4, the predominant water pore in brain (Hiroaki, et al. (2006) *J. Mol. Biol.* 355:628-639), and hAQP5 (Horsefield, et al. (2008) *Proc. Natl. Acad. Sci. USA* 105:13327-13332).

Thirteen WCPs have been described in mammals; seven are aquaporins (AQP0, AQP1, AQP2, AQP4, AQPS, AQP6, and AQP8), four are aquaglyceroporins (AQP3, AQP7, AQP9, and AQP10), whereas AQP11 and AQP12 are "superaquaporins" or subcellular AQPs. The characteristics, distribution, functions and some pathological implications of individual mammalians WCPs have been described (Takata, et al. (2004) *Prog. Histochem. Cytochem.* 39:1-83; King, et al. (2004) *Nat. Rev. Mol. Cell. Biol.* 5:687-698). In addition, the amino acid and nucleotide sequence of these WPCs are readily available from sources such as PubMed, Genbank, and Uniprot. For example, the protein sequences for human AQP0, AQP1, AQP2, AQP3, AQP4, AQPS, AQP6, AQP7, AQP8, AQP9, AQP10, AQP11 and AQP12 are respectively available under GENBANK Accession Nos. NP_036196.1, NP_932766.1, NP_000477.1, NP_004916.1, NP_001641.1, NP_001642.1, NP_001643.2, NP_001161.1, NP_001160.2, NP_066190.2, NP_536354.2, NP_766627.1, and NP_945349.1. Expression of one or more WPCs in a producer cell results in increased levels of WPCs in EVs obtained from said producer cells. Increased levels of WPCs on EV surfaces facilitates EV volume control via water permeation, thereby leading to enhanced EV transport through matrices/tissues and/or deeper penetration into target tissues.

The preparation of a recombinant producer cell to harbor and express a nucleic acid construct encoding the one or more water channel proteins can be carried out by conventional recombinant protein expression methods using commercially available expression vectors (e.g., plasmid or viruses) under the control of suitable regulatory sequences (e.g., promoters, enhancers, terminators, and the like).

As demonstrated herein, EVs encapsulated in a matrix and exposed to a hypertonic medium, such as 3% polyethylene glycol, resulted in an increase in EV release. Similarly, ion channel inhibitors, in particular selective cation channel inhibitors such as tetrodotoxin and GsMTx4 increased EV release in hydrogels. Thus, cell volume mediated by water channel protein activity can be modulated (decreased) by responses to osmotic stresses such as hypertonic medium or one or more ion channel inhibitors. Accordingly, the activity of one or more water channel proteins on the surface of EVs can be modified by non-recombinant approaches. In some aspects, the activity of the one or more water channel proteins is modified by exposing the EVs to a hypertonic medium or one or more ion channel inhibitors.

In other embodiments, the population of producer cells has been modified by exposure to environmental conditions (e.g., hypoxia), small molecule addition, presence/absence of exogenous factors (e.g., growth factors, cytokines) at the time, or substantially contemporaneous with, isolating the plurality of EVs thereby modifying the composition of the EVs. For example, one may add a differentiation agent to a population of stem cells, progenitors and/or precursors to promote partial or full differentiation of the cell, and thereafter derive a plurality of EVs. In various embodiments, altering the regulatory state of the cell changes composition of one or more EVs in the plurality of EVs.

This invention also provides a composition including EVs encapsulated in a matrix. A "matrix" refers to biocompatible, biodegradable matrix or hydrogel that is preferably artificially produced. "Biocompatible" generally refers to a material and any metabolites or degradation products thereof that are generally non-toxic to the recipient and do not cause any significant adverse effects to the subject. "Biodegradable" generally refers to a material that will degrade or erode by hydrolysis or enzymatic action under physiologic conditions to smaller units or chemical species that are capable of being metabolized, eliminated, or excreted by the subject. The degradation time is a function of polymer composition and morphology.

Matrices of use in this invention can be produced with natural or synthetic polymers, or a combination thereof. In this respect, matrices of this invention include artificial extracellular matrices (ECMs) and hydrogels. In some aspects, the matrix is an artificial extracellular matrix (ECM) including one or more natural polymers that provides a cell-adhesive substrate, control of three-dimensional tissue structure, and/or presentation of growth factors, cell-adhesion signals, and mechanical signals. Artificial ECMS are typically composed of proteoglycans, glycoproteins, and glycosaminoglycans found in a natural tissue, which may be crosslinked to modulate stiffness. Examples of suitable polymers for preparing artificial ECMS include, but are not limited to, hyaluronic acid, cellulose, poly(hydroxyalkanoate), silk, gelatin, collagen, fibrin, alginate, chitosan, and a combination thereof.

In other aspects, the matrix is a hydrogel. A "hydrogel" refers to a substance formed when an organic polymer is crosslinked via covalent, ionic, and/oor hydrogen bonds to create a three-dimensional open-lattice structure which entraps water molecules to form a gel. The encapsulated EV typically have a larger diameter than the average mesh size of the hydrogel. Examples of materials which can form hydrogels include polylactic acid, polyglycolic acid, PLGA polymers, alginates and alginate derivatives, agarose, pectin, natural and synthetic polysaccharides, polyamino acids such as polypeptides particularly poly(lysine), polyesters such as polyhydroxybutyrate and poly-epsilon.-caprolactone, polyanhydrides; polyphosphazines, poly(vinyl alcohols), poly (alkylene oxides) particularly polyethylene oxides), poly (allylamines) (PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

In some aspects, the hydrogels are crosslinked physically through divalent cations or covalently through click chemistry, thereby providing for a tunable complex modulus G*. Physical crosslinking leads to stress relaxing hydrogels and covalent crosslinking leads to elastic hydrogels. For purposes of this invention, a G* of about 500 Pa is deemed to be 'soft' and G* of about 3,000 Pa as 'stiff'. Representative crosslinked hydrogels of the invention preferably have a complex modulus G* in the range of about 0.3 to about 3 kPa. The crosslinked hydrogels of the invention are nanoporous, like the decellularized matrix regardless of the cross-linking density or type. The crosslinked hydrogels possess a tunable range of stress relaxation behaviors. In certain embodiments, the half-time of stress relaxation or stress relaxation rate is between about 1 second and 200 seconds, or more preferably about 10 seconds and about 100 seconds.

In a certain embodiment, the hydrogel is alginate or modified alginate material. "Alginate" is a collective term used to refer to linear polysaccharides formed from (1-4)-linked β-D-mannuronic acid monomers (M units) and L-guluronic acid monomers (G units) in any M/G ratio and sequential distribution along the polymer chain, as well as salts and derivatives thereof. The alginate monomers may be ionically and/or covalently crosslinked. In certain embodiments, monomers are crosslinked with divalent or trivalent cation, e.g., $Ca^{2+}$, $Mg^{2+}$, $Sr^{2+}$, $Ba^{2+}$, $Be^{2+}$ and $Al^{3+}$. In a specific embodiment, the divalent cation is $Ca^{2+}$, $Sr^{2+}$ or $Ba^{2+}$.

In other embodiments, the alginate monomers are covalently crosslinked. Representative covalent crosslinking methods include strain-promoted azide-alkyne cycloaddition (SPAAC), and click chemical reactions including the inverse electron demand Diels-Alder reaction between tetrazine and trans-cyclooctene (TCO), dibenzocyclooctene (DBCO) and azide, and tetrazine and norbornene. See Desai, et al. (2015) *Biomaterials* 50:30-37 and references cited therein. One or a combination of ionic and covalent cross-linking can be used to modify the mechanical stability, stiffness, and/or utility of the hydrogel.

In certain aspects, an alginate of use in the preparation of the hydrogel of this invention has a molecular weight of greater than about 250 kDa (e.g., about 251 kDa, about 300 kDa, about 350 kDa, about 400 kDa, about 450 kDa or about 500 kDa). Preferably, an alginate of use in the preparation of the hydrogel of this invention has a molecular weight in the range of about 250 kDa to about 500 kDa.

In other embodiments, hydrogels interpenetrated with other natural matrices such as MATRIGEL® (the solubilized basement membrane matrix secreted by Engelbreth-Holm-Swarm (EHS) mouse sarcoma cells) and collagen may be prepared by mixing with the natural matrices in order to modulate (decrease) EV transport.

In another aspect, this invention is a method of EV therapy which involves administering to a subject in need of such treatment an effective amount of a composition composed of EVs encapsulated in a matrix, wherein the EVs have a modified number or activity of one or more water channel proteins compared to a wild-type EVs. As used herein, "subject" means an individual. Thus, subjects include, for example, domesticated animals, such as cats and dogs, livestock (e.g., cattle, horses, pigs, sheep, and goats), laboratory animals (e.g., mice, rabbits, rats, and guinea pigs) mammals, non-human mammals, primates, non-human primates, rodents, birds, reptiles, amphibians, fish, and any other animal. The subject is preferably a mammal such as a primate or a human. In some embodiments, the subject has one or more damaged or dysfunctional cells and/or tissues. In a certain embodiment, the subject is suffering from a lung injury. In particular embodiments, the lung injury is endotoxin-induced acute lung injury, infection-mediated lung injury, or fibrotic lung injury.

According to some embodiments, the encapsulated EVs can be used to treat a wide variety of cell types as well, including but not limited to immune cells, blood cells, vascular cells, epithelial cells, interstitial cells, musculature (skeletal, smooth, and/or cardiac), skeletal cells (such as bone, cartilage, and connective tissue), nervous cells (such as neurons, glial cells, astrocytes, Schwann cells), liver cells, kidney cells, gut cells, lung cells, skin cells or any other cell in the body.

Administration of the compositions of the disclosure will be via any common route so long as the target tissue is available via that route. Such routes include oral, nasal, buccal, rectal, vaginal or topical route. Ideally, administration may be by intratracheal instillation, intratracheal inhalation, intravenous delivery, intramuscular delivery, intraarterial delivery, topical delivery, renal artery injection, portal vein injection, intrabone delivery, intraarticular delivery, intralymphatic delivery, intrathymic delivery, intrarenal delivery, intracorneal delivery, intraportal delivery, intrahepatic delivery, or intracardiac injection of the encapsulated EVs. Such compositions would normally be administered as pharmaceutically acceptable compositions.

In some embodiments, the encapsulated EVs are delivered to and/or are taken up by damaged or dysfunctional cells and/or tissues. In several embodiments, administration of the therapeutic composition includes administration at a tissue or organ site that is the same as the target tissue. In some embodiments, administration of therapeutic composition involves administration at a tissue or organ site that is different from the target tissue. In some embodiments, administration of therapeutic composition includes administration systemically (e.g., in the blood).

In certain embodiments, administration involves providing to a subject about $10^2$, $10^4$, $10^6$, $10^7$, $10^8$, $10^9$, $10^{10}$, $10^{12}$, or more EVs. In several embodiments, a single dose of the therapeutic composition includes between about $1 \times 10^6$ and about $1 \times 10^9$ of the encapsulated EVs. In some embodiments, a single dose of the therapeutic composition is administered multiple times to the subject. The number of EVs administered may be chosen based on the route of administration and/or the severity of the condition for which the EVs are administered. In some embodiments, the administration of the therapeutic composition is inhalation or oral administration. In some embodiments, the therapeutic composition is administered by intra-arterial, intravenous, intratracheal, intrabone, or retrograde coronary sinus infusion or injection.

Tissues treated according the method provided herein include, in some embodiments, cardiac tissue, brain or other neural tissue, skeletal muscle tissue, pulmonary tissue, arterial tissue, and capillary tissue. In several embodiments, the tissue to be treated is damaged or dysfunctional is due to an injury, age-related degeneration, cancer, or infection. In some embodiments, the methods provided herein treat tissue that is damaged or dysfunctional due to an acute event or a chronic disease. In some embodiments, the acute event or chronic disease is as a result of myocardial infarction, traumatic head injury, and/or stroke. Non-limiting examples of additional chronic diseases that are treated include congestive heart failure, heart disease, ischemic heart disease, valvular heart disease, connective tissue diseases, HIV infection, dilated cardiomyopathy, myopathy, and dystrophinopathy (e.g., Duchenne muscular dystrophy), liver disease, sickle cell disease, dilated cardiomyopathy, infection such as Schistosomiasis, diabetes, Alzheimer's disease, Parkinson's disease, Huntington's disease, and Amyotrophic Lateral Sclerosis (ALS).

In additional aspects, encapsulated EVs are administered in conjunction with a therapeutic agent, e.g., an agent useful in treating the subject's disease or condition. The therapeutic agent is ideally within the lumen of the EVs and may include antibodies, proteins and peptides, nucleic acids, or small molecules.

Compositions containing the encapsulated EVs can be prepared by combining the encapsulated EVs with a pharmaceutically acceptable carrier or aqueous medium. The phrase "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and the like. The use of such media and agents for pharmaceutically active substances is well known in the art. Except insofar as any conventional media or agent is incompatible with the EVs of the present disclosure, its use in therapeutic compositions is contemplated. Pharmaceutical compositions can be determined by one skilled in the art depending upon, for example, the intended route of administration, delivery format and desired dosage. See, for example, Remington, J. P. & Allen, L. V. (2013) *Remington: The Science and Practice of Pharmacy*. London, Pharmaceutical Press.

The compositions of the invention can be incorporated in an injectable formulation. The formulation may also include the necessary physiologically acceptable carrier material, excipient, lubricant, buffer, surfactant, antibacterial, bulking agent (such as mannitol), antioxidants (ascorbic acid or sodium bisulfite) and the like.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials may include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA; complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as poloxamers, PEG, sorbitan esters, polysorbates such as polysorbate 20 and polysorbate 80, Triton', trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, Remington, J. P. & Allen, L. V. (2013) *Remington: The Science and Practice of Pharmacy*. London, Pharmaceutical Press.

The primary vehicle or carrier in a pharmaceutical composition may be either aqueous or nonaqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefore. Pharmaceutical compositions of the invention may be prepared for storage by mixing the selected composition having the desired degree of purity with optional formulation agents (Remington's Pharmaceutical Sciences, Id.) in the form of a lyophilized cake or an aqueous solution.

The composition can be provided by sustained release systems, e.g., implantation devices. The compositions may be administered by bolus injection or continuously by infusion, or by implantation device. Where an implantation device is used, the device may be implanted into any suitable tissue or organ. The injections may be given as a one-time treatment, repeated (daily, weekly, monthly, annually etc.) in order to achieve the desired therapeutic effect.

The compositions of the invention can be delivered parenterally. When parenteral administration is contemplated, the therapeutic compositions for use in this invention may be in the form of a pyrogen-free, parenterally acceptable aqueous solution. A particularly suitable vehicle for parenteral injection is sterile distilled water. Preparation can involve sustained release of the EVs, which may then be delivered via a depot injection. Formulation with hyaluronic acid has the effect of promoting sustained duration in the circulation. Implantable drug delivery devices may be used to introduce the desired composition.

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like.

Supplementary active ingredients also can be incorporated into the compositions. The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intraperitoneal, or intravenous injection. Such compositions would normally be administered as pharmaceutically acceptable compositions.

As used herein, the term "amount effective," "effective amount" or a "therapeutically effective amount" refers to an amount of the EVs or composition of the invention sufficient to achieve the desired result. The amount of the EVs or composition which constitutes an "effective amount" or "therapeutically effective amount" may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect.

Although not precluded, treating a disease or condition does not require that the disease, condition, or symptoms associated therewith be completely eliminated, including the treatment of acute or chronic signs, symptoms and/or malfunctions. "Treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. "Treatment" therefore also includes relapse prophylaxis or phase prophylaxis. The term "treat" and synonyms contemplate administering a therapeutically effective amount of the EVs of the invention to an individual in need of such treatment. A treatment can be orientated symptomatically, for example, to suppress symptoms. Treatment can be carried out over a short period, be oriented over a medium term, or can be a long-term treatment, for example within the context of a maintenance therapy.

The following non-limiting examples are provided to further illustrate the present invention.

EXAMPLE 1

Preparation of Encapsulated EVs in Alginate Hydrogels

Particle Size and Number Characterization. Particle size and number were obtained using a Nanoparticle Tracking Analysis 3.2 via a NanoSight NS300 (Malvern) with a 405 nm laser. Samples were introduced by a syringe pump at a rate 100 µl min$^{-1}$. Three 30 second videos were acquired using camera level 14 followed by detection threshold 7. Camera focus, shutter, blur, minimum track length, minimum expected particle size and maximum jump length were set automatically by the software. Samples were diluted as needed to maintain particles per video from 100 to 2,000.

Cell Culture. All cells were cultured at 37° C. in 5% $CO_2$. HeLa cells (ATCC), D1 MSC cells (ATCC), and HEK293T cells (ATCC) were cultured using high-glucose Dulbecco's Modified Eagle Medium (DMEM, Thermo Fisher Scientific) supplemented with 10% fetal bovine serum (FBS, Atlanta Biologicals), 1% penicillin/streptomycin (P/S; Thermo Fisher Scientific) and 1% GlutaMAX ,(Thermo Fisher Scientific) to 80% confluency before passaging, no more than 30 times. Human umbilical vein endothelial cells (HUVEC, Lonza) were cultured using Ham's F-12K medium (Thermo Fisher Scientific) supplemented with 10% FBS, 1% P/S, 1% GlutaMAX, 0.1 mg/ml heparin (Sigma) and endothelial cell growth supplement (Sigma) at passage 5. Human MSCs (hMSCs) were derived by the plastic adherence of mononucleated cells from human bone marrow aspirate (Lonza). After 3 days, the adherent cells were cultured in hMSC medium: α-minimal essential medium (Thermo Fisher Scientific) supplemented with 20% FBS, 1% P/S (Thermo Fisher Scientific) and 1% GlutaMAX (Thermo Fisher Scientific). After reaching 70-80% confluence at 10-14 days, the cells were split, expanded in hMSC medium and used at passage 3. Cells were routinely tested for mycoplasma contamination and only used if no contamination was present.

Lentiviral Expression of CD63 Fused with Katushka2S (K2S). A DNA plasmid that contained K2S, a far-red fluorescent protein, was synthesized in a pUC57-Kan backbone (GenScript). The K2S sequence was cloned into a lentiviral construct that contained CD63 (Applied Biological Materials) so that K2S fused to CD63 on the C-terminus of CD63. D1 MSCs were transduced with lentivirus that contained the CD63-K2S plasmid using standard techniques (McGinley, et al. (2011) *Stem Cell Res. Ther.* 2:12). Briefly, lentiviral particles were produced with a second-generation lentiviral packaging system (Applied Biological Materials) using Lentifectin (Applied Biological Materials) in HEK293T cells. Lentiviral particles were purified and applied to D1 MSCs at passage 10 with 8 µg/ml polybrene (Sigma) for 3 days. Cells were expanded over a period of several days to reach ~80% confluency. Subsequently, cells were sorted using a MoFlo Astrios (Beckman Coulter) based on their CD63-K2S signal compared to those of non-transduced cells of the same passage. Concentrated EV solutions were shown to be positive for CD63-K2S versus EVs from non-transduced cells using IVIS imaging (Living Image 4.0, Perkin Elmer).

Extracellular Vesicle Isolation and Preparation. To isolate EVs from cells, the cells were washed twice with Hank's balanced salt solution (HBSS, Thermo Fisher Scientific) followed by incubation with serum-free growth medium for 1 hour. Subsequently, the medium was exchanged with a medium composed of high-glucose DMEM supplemented with 10% exosome-depleted FBS (Thermo Fisher Scientific) instead of 10% FBS. The next day, the medium was centrifuged at 2,000 g for 10 minutes to remove cellular debris followed by centrifugation at 10,000 g to remove particles larger than 500 nm (Lobb, et al. (2015) *J. Extracell. Vesicles* 4:27031). The medium was added to a 100 kDa molecular weight (MW)-cutoff column (Amicon) and centrifuged at 5,000 g for 20 minutes followed by washing with an equal volume of HBSS. The retentate was resuspended and confirmed to contain concentrated EVs using NanoSight NS300 (Malvern).

Lyophilization of EVs. Concentrated EVs were frozen at −80° C. overnight. If applicable, the preparations were treated with 4% trehalose (Sigma) before freezing. They were then placed in a lyophilization chamber operating at <0.1 mbar vacuum and <−100° C. temperature and allowed to sublimate overnight. The solid was reconstituted in HESS and confirmed to contain EVs using NanoSight NS300.

Decellularization of Lung Tissues. All animal procedures were performed in compliance with National Institutes of Health and institutional guidelines. Female C57BL/6 J mice were purchased from The Jackson Laboratory, housed in the laboratory and killed 12 weeks after birth. Lung tissue was harvested and decellularized based on established techniques (Bonenfant, et al. (2013) *Biomaterials* 34:3231-3245). Briefly, the heart-lung bloc was exposed and the trachea cannulated with a blunted 18-gauge needle. Lungs were infused with 1 ml of deionized water that contained 5% P/S (wash solution). The heart-lung bloc was excised and washed through the airway and the right ventricle, incubated in a 0.1% Triton™-X wash solution overnight at 4° C., washed and incubated in a 2% sodium deoxycholate wash solution overnight at 4° C. The tissue was then washed, incubated in a 1 M NaCl wash solution for 1 hour at room temperature, washed and incubated in a wash solution that contained DNAase for 1 hour at room temperature. The tissue was placed in a solution of liquified 5% low-melting-point agarose (GeneMate) and allowed to solidify at 4° C. overnight. Slices were prepared using a tissue slicer (Braintree) into 1 mm sections and punched into 5 mm discs using a punch (Integra). Discs were placed in HBSS, incubated at 42° C. for 30 minutes and washed several times.

Multiphoton Microscopy. About $1 \times 10^9$ CD63-K2S EVs were incubated with a ~5 mm tissue slice at 37° C. for 3 days followed by washout. EV-loaded tissue slices were imaged using a X20 1.00 NA water immersion objective (Olympus) with a multiphoton microscope (Bruker Fluorescence Microscopy) equipped with a Coherent Cameleon Ultra II laser that employed both second harmonic and two-photon excited fluorescence signal generation (Pena, et al. (2007) *Microsc. Res. Tech.* 70:162-170). Backward-scattering second harmonic generation was obtained at 860 nm excitation to capture signals from collagen within tissue and two-photon excited fluorescence generation was performed at 760 nm excitation to capture signals from CD63-K2S. Three images were taken each for experimental and background (no loaded EVs) conditions. Images were processed by subtracting background fluorescence from the 760 nm channel. Then, three regions of interest were chosen for each background-subtracted image and Pearson's correlation coefficient was calculated. Next, the 760 nm channel signal was randomized using the MATLAB function RAND-BLOCK, Pearson's correlation coefficient calculated again and the distributions compared.

Lung-Tissue Transport Experiments. After loading $~1 \times 10^9$ CD63-K2S EVs onto a ~5 mm tissue slice for 3 days, the loading was confirmed using IVIS. The EV transport was determined by measuring tissue fluorescence before and after the indicated times. Imaging occurred with a 3-second exposure using a fluorescence excitation filter at 570 nm and an emission filter at 640 nm. IVIS software (Living Image 4.0, Perkin Elmer) was used to create a region of interest around the tissue pieces where the total fluorescent signal was counted.

Material Preparation and Hydrogel Formation. Raw sodium alginates with different molecular weights, low (5/60, ~40 kDa) and medium (10/60, ~120 kDa), were obtained from FMC Corporation. Alginate was purified through dialysis in a 3.5 kDa membrane submerged in water, followed by treatment with activated charcoal (Sigma, 0.5 g per gram alginate). The alginate was then filtered, frozen and lyophilized to obtain a solid polymer. Conjugation of click chemistry reagents or RGD (amino acid sequence GGG- GRGDSP (SEQ ID NO:1), Peptide 2.0) to alginate polymers was performed using an established method (Desai, et al. (2015) *Biomaterials* 50:30-37). 1-Bicyclo[2.2.1]hept-5-enylmethanamine (norbornene amine, Matrix Scientific) was conjugated to 10/60 alginate at degree of substitution (DS) 75-150 and tetrazine-amine (Conju-Probe) was conjugated to 5/60 alginate to achieve a DS18-36. For some experiments, RGD was conjugated to 10/60 alginate at DS10. Physically crosslinked hydrogels were formed according to established methods (Chaudhuri, et al. (2015) *Nat. Commun.* 6:6365). Briefly, alginate solutions were mixed to be 1% 5/60 and 1% 10/60 (2% total), added to a syringe and locked to another syringe with $CaSO_4$ (Sigma) to achieve final calcium concentrations of 12 mM (soft) and 20 mM (stiff). After mixing, the solutions were deposited under glass for 2 hours to form a hydrogel. For covalently crosslinked hydrogels, tetrazine-alginate and norbornene-alginate were mixed to be 1% each (2% total) and deposited under glass for 2 hours to form a hydrogel. Interpenetrating network hydrogels of collagen-1 and alginate were created as previously described (Branco da Cunha, et al. (2014) *Biomaterials* 35:8927-8936). Briefly, hydrogels were prepared as physically crosslinked hydrogels, but the solution was mixed with collagen-I to achieve a final concentration of 0.75 or 0.375 mg/mL before mixing with $CaSO_4$. To avoid drying, hydrogels were incubated in a 'retention medium': HEPES-buffered saline at pH 7.75 supplemented with 2 mM $CaCl_2$, an amount shown previously to prevent the leaching of calcium from hydrogels without leading to further crosslinking (Lee & Mooney (2012) *Prog. Polym. Sci.* 37:106-126).

Mechanical Characterization of Hydrogels and Tissues. The mechanical properties of hydrogels or tissues were obtained using rheometry via Anton Paar MCR302. Storage (G') and loss (G") moduli were measured through a frequency sweep by lowering the geometry (Anton Paar PP08) to a 5% normal strain followed by a rotation that induced a 0.5% shear strain at an increasing frequency and finally measurement of the resulting shear stress. The complex shear modulus G* was calculated (Hosford (2005) *Mechanical Behavior of Materials*, Cambridge Univ. Press):

$$G^* = \sqrt{G'^2 + G''^2} \tag{1}$$

The loss tangent was defined as:

$$\tan\delta = G'' / G' \tag{2}$$

To determine the stress relaxation, the geometry was lowered at constant velocity (25 μm/s) through the linear elastic region until a 15% strain was reached. Swelling ratios were calculated by leaving samples to dry or swell overnight followed by mass measurements. The swelling ratio Q was calculated through the volumes of hydrogels expressed as (Carr & Peppas (2009) *Macromol. Biosci.* 9:497-505; Berger, et al. (2004) *Eur. J. Pharm. Biopharm.* 57:19-34):

$$V_s = \frac{m_d}{m_s} = \frac{1}{Q}; V_r = \frac{m_d}{m_r} \tag{3}$$

where m is the hydrogel weight and subscripts d, r and s denote dry, relaxed (before swelling) and swollen hydrogels, respectively. The average molecular weight between the crosslinks was calculated as:

$$1/\overline{M}_c = 2/\overline{M}_n - \frac{(\overline{v}/V)\left[\ln(1 - V_S) + V_S + \chi V_S^2\right]}{V_r\left[(V_S/V_r)^{\frac{1}{3}} - V_S/2V_r\right]} \tag{4}$$

with $\overline{M}_n$ is the average molecular weight of polymers, $\overline{v}/V$ the molar volume of hydrogel divided by the molar volume of water and $\chi$ the Flory interaction parameter. The values were used to calculate the average hydrogel mesh size through the equation:

$$\xi = V_S^{-\frac{1}{3}}\left(\frac{2C\overline{M}_C}{\overline{M}_r}\right)^{\frac{1}{2}} l \tag{5}$$

with C the polymer characteristic ratio, $\overline{M}_r$ the average molecular weight of the polymer repeating unit and 1 the carbon-carbon bond length. Differential scanning calorimetry was used to perform thermoporometry to measure the pore size distributions according to known methods (Boontheekul, et al. (2005) *Biomaterials* 26:2455-2465). Briefly, samples ~10 mg were placed in a sealable aluminum pan inside the differential scanning calorimetry instrument (TA Instruments Q2000). Samples were cooled to −30° C. at a rate of 4° C./minute, held for 5 minutes, warmed to 15° C. at a rate of 4° C./minute, held for 5 minutes and then cooled again to −30° C. at 4° C./minute. Distributions were calculated by determining $\Delta V/\Delta R_p$ (Iza, et al. (2000) *Polymer* 41:5885-5893), where $R_p$ is the pore radius, and then fitted to a frequency-normalized histogram.

Bulk Transport Experiments. Liposomes (FormuMax) were obtained with a similar (~45% cholesterol, ~55% phospholipids) content as that of the EVs (Skotland, et al. (2019) *J. Lipid Res.* 60:9-18). The encapsulation of particles or dextran in bulk alginate hydrogels was performed by mixing particles with alginate or click alginate followed by hydrogel formation. The hydrogels were punched into discs and placed into polystyrene plates with retention medium. If applicable, the hydrogels were treated with blebbistatin (Cayman) or Y-27632 (Cayman). If necessary, gels were digested by adding medium with 3.4 mg/ml alginate lyase (Sigma) and placing at 37° C. for 30 minutes. Release was measured using fluorescence for polystyrene nanoparticles (SpheroTech) and FITC-dextran (500 kDa, Sigma). Percent release was determined at the indicated times as the number of particles in the medium $P_M$ divided by $P_M$ plus the number of particles in the digested hydrogel $P_G$ as:

$$\% \text{ Release} = \frac{P_M}{P_M + P_G} \times 100\% \tag{6}$$

For EVs and liposomes, $P_M$ was measured as above using NanoSight NS300, but $P_G$ was determined by calculating the initial number of particles added to the hydrogel using NanoSight NS300. Samples without encapsulated particles were used to account for background.

3D Single-Particle Tracking. CD63-K2S EVs were encapsulated in hydrogels, placed on dishes of no. 1.5 coverslip thickness (MatTek), and imaged at ×60 with immersion oil of refractive index 1.518 (Cargill) using a DeltaVision OMX microscope (GE). Single channel 1024×1024 pixel (81.92× 81.92 µm) images were obtained in 2 µm thick stacks with 0.125 µm spacing (16 images per stack) using the conventional imaging mode. Over ~8 seconds, 30 stacks were acquired for a stack frequency of 3.75 Hz and image frequency of 60 Hz. After acquisition, the images were processed through deconvolution using softWoRx. Using the IMARIS 'Spots' function, a custom particle tracking algorithm was created. Particles were determined using intensity thresholding over regions that measured 10×10×1 pixels followed by tracking their 3D position (x, y, z) over time (t). Tracks could continue if the particle was undetectable for a single timepoint within the track but not for two or more consecutive timepoints.

Analysis of Particle-Tracking Data. Mathematical calculations and analysis were performed using MATLAB software. The particle mean square displacement (MSD) was calculated from the positional data as:

$$MSD(t) = x(t) - x(t = 0[]^2 + y(t) - y(t) = 0)]^2 + z(t) - z(t[ = 0[^2 \quad (7)$$

Tracks with less than five measurements of MSD were removed from further analysis. For ensemble-averaged tracks, a lower limit of 20 points and an upper limit of 30 points were defined to constrain the tracks considered for analysis, as uneven track sizes can bias the results (Etoc, et al. (2018) *Nat. Mater.* 17: 740-746). Owing to this, the data are shown only up to the lower limit of 20 points (t≈5 seconds). To account for static (or localization) error (Backlund, et al. (2015) *Phys. Rev. E.* 91:062716) for each particle type, particles were adhered to glass using (3-aminopropyl) trimethoxysilane (Sigma) using a conventional method (Vorselen, et al. (2018) *Nat. Commun.* 9:4960). The MSD was tracked for adherent particles over time, and the static error was defined as the plateau MSD. This error was subtracted from all subsequent MSD measurements for each experimental group.

Ensemble-averaged track data were generated by averaging the MSD for each track i at every time t elapsed since the start of tracking:

$$MSD\left(t\left\langle\frac{1}{N}\sum_{i=1}^{N}MSD_i(t)\right\rangle\right) = \quad (8)$$

where N is number of tracks. Exponent α was calculated for ensemble-averaged tracks using the following equation:

$$MSD(t\langle_a\rangle)t^\alpha \quad (9)$$

Diffusion coefficient $D_{1.06s}$ was calculated over intervals τ=4Δt≈1.06 s for each track, as in the following equation:

$$D_{1.06s} = MSD(\tau = 1.06s)/6(1.06s) \quad (10)$$

Thus, if the total track time is T, a given track has T/τ values for $D_{1.06s}(\tau)$, which were averaged to provide a singular value for $D_{1.06s}$ for a given track. The expected $D_{1.06s}$ for particles was determined based on the Stokes-Einstein relationship:

$$D = \frac{k_B T}{6\pi\eta r} \quad (11)$$

where $k_B T$ is the Boltzmann constant multiplied by temperature, r is the particle radius and η is the solution viscosity. The viscosity of glycerol solutions was determined according to known methods (Segur & Oderstar (1951) *Ind. Eng. Chem.* 43:2117-2120). The degree of heterogeneity of $D_{1.06s}$ was defined as described herein. For each sample, simulations were performed to obtain an equal number of simulated tracks as the number of tracks measured for each sample. Each MSD(t) was drawn randomly from a zero-mean Gaussian distribution determined for each sample with variance $2D_{1.06s}t$ (Etoc, et al. (2018) *Nat. Mater.* 17:740-746). $D_{1.06s}$ was then calculated for simulated tracks as for experimental measurements:

$$D_\tau = MSD(\tau)/6\tau \quad (12)$$

'Cages' of confinement were defined elsewhere herein. Tracks were evaluated for their ability to overcome this cage size by exceeding c (particles escaping) or not (particles not escaping). The timepoint at which the particle exceeds c is defined as the escape time. $R_g$ was defined as the time-averaged root mean square displacement of particle tracks as:

$$R_g = \left[1/N\sum_{i=0}^{N}MSD(t_i)\right]^{\frac{1}{2}} \quad (13)$$

over each measured timepoint $t_i$ through the duration of the track.

ATP Measurement and Pharmacological Depletion. ATP concentration was measured using a commercially available luciferase-based assay (Cayman). Briefly, samples were lysed followed by the addition of a mixture that catalyzes a reaction to produce bioluminescence based on the concentration of ATP within the samples. Values of bioluminescence were compared to a standard curve with a known concentration of ATP. To deplete ATP, the cells were treated with 1 µg/ml oligomycin (Cayman) and 1 mM 2-deoxy-D-glucose (Cayman) for 24 hours.

siRNA Transfection. Scrambled siRNA (Dharmacon) or siRNA against AQP1 (Ambion) was diluted to 160 nM in unsupplemented Opti-MEM medium (Thermo) and combined 1:1 with OPTI-MEM® culture medium supplemented with 2% LIPOFECTAMINE® RNAiMAX® transfection reagent (Thermo Fisher Scientific) and incubated at room temperature for at least 20 minutes. Cells were washed with HBSS and fresh growth medium was added to cells. The transfection solution was added dropwise for a final siRNA concentration of 4 nM and cells were incubated for 3 days followed by EV isolation.

Gene Expression Analysis. TRIZOL® Reagent (guanidinium thiocyanate, Thermo Fisher Scientific) was added directly to cells. Chloroform (200 µl) was added per 1 ml of TRIZOL® Reagent followed by centrifugation for 15 minutes at 15,000 r.p.m. and 4° C. The top layer was collected and RNA precipitated with 500 µl of isopropanol for 20 minutes at 4° C. Samples were centrifuged at 12,500 r.p.m. for 15 minutes at 4° C. The supernatant was removed, precipitated RNA was washed with 75% EtOH and centrifuged for 5 minutes at 7,500 r.p.m. and 4° C. EtOH was removed and the purified RNA was resuspended in 15 µl of RNase-free water. The RNA concentration was quantified by NanoDrop. Complementary DNA was reverse transcribed by SUPERSCRIPT® III reverse transcriptase (Thermo Fisher Scientific). qPCR was performed in the ViiA7 qPCR system with PowerSYBR Green master mix (Applied Biosystem). Samples were analyzed in triplicate with 50 ng of complementary DNA per well. Relative gene expression was computed by the delta-delta threshold cycle method by comparing threshold cycle values to those of a reference gene (GAPDH). Table 1 shows the list of primers for qPCR.

TABLE 1

| Target | Primer  | Sequence             | SEQ ID NO: |
|--------|---------|----------------------|------------|
| GADPH  | Forward | ACATCGCTCAGACACCATG  | 2          |
|        | Reverse | TGTAGTTGAGGTCAATGAAGGG | 3        |
| AQP1   | Forward | CTGGCGATTGACTACACTGG | 4          |
|        | Reverse | AAGTCATAGATGAGCACTGCC | 5         |
| AQP2   | Forward | TTGGTTTCTCTGTTACCCTGG | 6         |
|        | Reverse | AACGGGCTGGATTCATGG   | 7          |
| AQP3   | Forward | CTTTGCCACCTATCCCTCTG | 8          |
|        | Reverse | CCACAGTGAAAGCCTCCAG  | 9          |
| AQP4   | Forward | GCTTAGATCTGGCTTTCAAAGG | 10       |
|        | Reverse | AATGTCCACACTTACCCCAC | 11         |
| AQP5   | Forward | CTCCCCAGCCTTATCCATTG | 12         |
|        | Reverse | ACCCAGAAGACCCAGTGAG  | 13         |

Atomic Force Microscopy. Vesicles were adhered to freshly cleaved mica by incubation at room temperature for 15 minutes followed by washing (Vorselen, et al. (2018) *Nat. Commun.* 9:4960). Atomic force microscopy was performed using an MFP-3D-Bio model (Asylum Research) with a pyramidal tip (Bruker; MLCT, triangular, resonant frequency ~125 kHz) according to known methods (Guo, et al. (2018) *Nat. Commun.* 9:130). Briefly, vesicles with a size range between about 50 and 300 nm were found by scanning in a tapping (a.c.) mode and indented until they reached 0.5 nN at 250 nm/s to generate a force-displacement curve. The data were analyzed and converted to Young's modulus (E) using MATLAB by modelling the EVs as thin elastic shells (Calò, et al. (2014) *Nanoscale* 6:2275-2285). The slope of the approach curve was calculated over a sliding interval and the surface of the vesicle was determined by a high and sustained change in the slope. The linear region was used to calculate E via the equation:

$$F(\delta) = \frac{aEt^2}{r}\delta \qquad (14)$$

with F as the measured cantilever force and $\delta$ as the tip displacement. The constant $at^2/r$ is determined by the vesicle geometry and assumed to be ~0.87 nm.

Western Blot. Western blot was performed using conventional methods on samples prepared by RIPA buffer. For each lane, 20 µg of protein was added. Immunoblots were performed against AQP1 (SCBT, 1:2000) and GAPDH (Proteintech, 1:5000) using an anti-rabbit or anti-mouse HRP-conjugate secondary antibody (Jackson ImmunoResearch Laboratories) combined with Luminol (Santa Cruz) substrate for detection.

Statistical Evaluation. Statistics were performed as described herein. All statistical analyses were performed using GraphPad Prism version 8.1.1. Unless otherwise noted, the statistical comparisons were made from at least three independent experiments by one-way ANOVA followed by Tukey's multiple comparison test, and then were considered significant if P<0.05.

EXAMPLE 2

EV Transport

To evaluate the extent to which EVs transport through the interstitial extracellular matrix (ECM), EVs were engineered from mouse mesenchymal stromal cells (MSCs) to contain the EV marker CD63 fused with far-red fluorescent protein K2S (Luker, et al. (2015) *Sci. Rep.* 5:10332) to visualize the EVs after passive loading by incubation in a decellularized matrix from lung tissue. MSCs were chosen as the source of EVs because in vivo they are often present in interstitial regions surrounded by matrix (Rakian, et al. (2015) *Stem Cell Res. Ther.* 6:235). The expression of CD63-K2S in EVs (K2S-EVs) did not alter their expected size distribution (diameter (d) 50-150 nm). Multiphoton second harmonic imaging analysis showed that the EVs were distributed throughout the collagen fibers within the matrix. Despite a nanoscale mean porosity of the matrix, ~50% of the loaded CD63-K2S-EVs were released from the matrix within ~24.7 hours, which indicated that EVs readily transport through naturally-derived nanoporous matrices. Further, EVs from K2S-CD63+MSCs can be detected in lungs in vivo. In particular, mice were treated for 4 hours i.p. with LPS (10 mg/kg) and subsequently provided i.t. with $5 \times 10^9$ EVs in a matrix. Quantification of K2S signals in lungs indicated approximately 2.8±0.3 K2S+ signal per $cm^2$.

Figure 2:
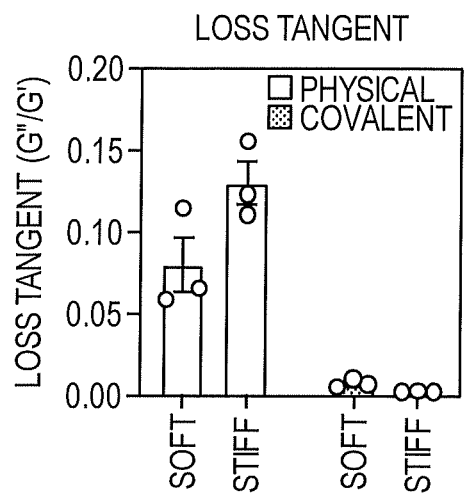
FIG. 2 shows loss tangent of the hydrogels calculated at 1 Hz. The data represent the mean of N=3 hydrogels. Error bars are s.e.m.
Figures 3, 4, 5:
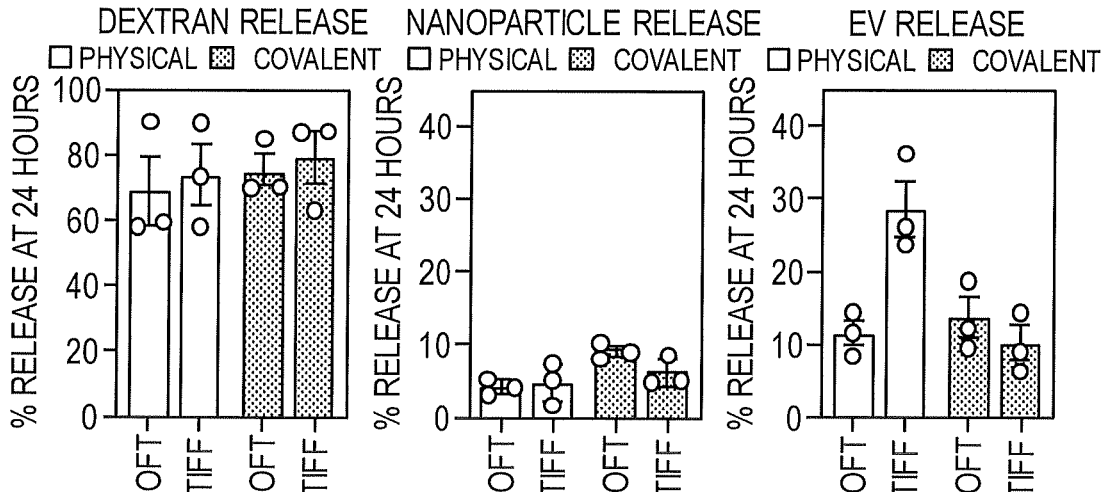
FIG. 3 shows 500 kDa dextran release from hydrogel at hours. N=3 hydrogels across 3 independent experiments. Data represent the mean and error bars denote the s.e.m.
FIG. 4 shows nanoparticle release from hydrogels at hours. N=3 hydrogels across 3 independent experiments. Data represent the mean and error bars denote the s.e.m.
FIG. 5 shows EV release from hydrogels at 24 hours. N=3 hydrogels across 3 independent experiments. Data represent the mean and error bars denote the s.e.m. *P=0.0095 via two-way analysis of variance (ANOVA) followed by Tukey's test for multiple comparisons.
Figure 6:
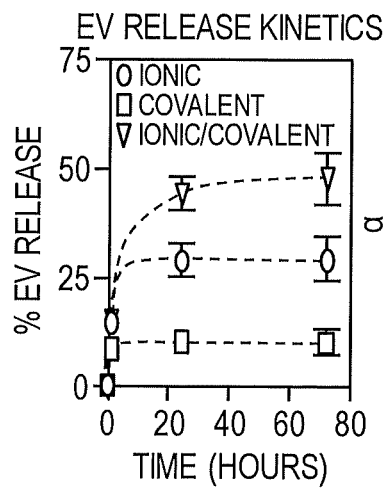
FIG. 6 shows the EV release kinetics from hydrogels. Ionic (physical crosslinking, stress relaxing hydrogels) show greater EV release than covalent (elastic hydrogels). Hydrogels of mixed crosslinking show with slightly delayed kinetics. All hydrogels are stiff. N=3 experiments.

A decellularized matrix exhibited a complex shear modulus magnitude G* of ~750 Pa with a loss tangent (viscous modulus/elastic modulus, G"/G') of ~0.15, and a stress relaxation behavior ($t_{1/2}$15 s). To determine whether the matrix mechanics mediates the EV transport, alginate-based hydrogels were engineered with a range of mechanical properties known to be present in tissues (Vining, et al. (2019) *Biomaterials* 188:187-197). Importantly, alginate-based hydrogels are bioinert, nondegradable and exhibit homogeneous nanoporous structures (Lee & Mooney (2012) *Prog. Polym. Sci.* 37:106-126), which makes them ideal to model ECM without the influence of biochemical or degrading interactions. Hydrogels can be crosslinked physically through divalent cations or covalently through click chemistry, and G* is tunable for both (FIG. 1). Physical crosslinking leads to stress relaxing hydrogels and covalent crosslinking leads to elastic hydrogels, as indicated by the loss tangent (FIG. 2) and stress relaxation times (Chaudhuri, et al. (2016) *Nat. Mater.* 15:326-334). As used herein G*≈500 Pa was deemed to be 'soft' and G*≈3,000 Pa as 'stiff'. Alginate-based hydrogels are nanoporous, like the decellularized matrix, regardless of the crosslinking density or type. This is consistent with the egg-box model of crosslinking between alginate chains (Grant, et al. (1973) *FEBS Lett.* 32:195-198), in which increased crosslinking is not expected to dramatically alter the mesh size. As expected, after dextran-FITC (hydrodynamic radius ~15 nm (Armstrong, et al. (2004) *Biophys. J.* 87:4259-4270)) molecules were encapsulated in the hydrogels, most released completely within 24 hours (FIG. 3). In contrast, a minimal release was observed for polystyrene nanoparticles (NPs; d≈80-100 nm) (FIG. 4). As for decellularized tissue, some EVs released from the hydrogels; however, surprisingly, EV release was greater from stress relaxing hydrogels with a higher G* (FIG. 5). This effect occurred for EVs from other cells as well indicating generalizability across cell type. Liposomes with a similar size and lipid content as EVs (Skotland, et al. (2019) *J. Lipid Res.* 60:9-18) did not exhibit a higher release from stress relaxing hydrogels with a higher G*. Hydrogels did not undergo degradation or loss of mass over the tested time period, which confirms the independence of degradation. Importantly, this observation is independent of $Ca^{2+}$, as treatment with ionomycin or EGTA did not affect the release. To test whether the EV release is mechanosensitive in a more natural ECM composition, an interpenetrating network hydrogel of alginate and collagen-I polymers was fabricated (Branco da Cunha, et al. (2014) *Biomaterials* 35:8927-8936) in which the hydrogel G* was tunable independent of the collagen-I concentration. Although EV release from the interpenetrating network was generally lower, depending on the collagen concentration, the release remained mechanosensitive. Furthermore, the kinetics of EV release from stiff hydrogels was investigated with ionic, covalent, or mixed crosslinking (FIG. 6). This analysis indicated that mixed crosslinking (ionic and covalent) increases EV release amount compared to covalent.

Figure 7:
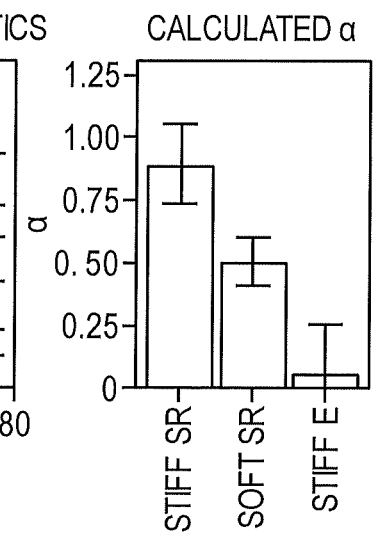
FIG. 7 shows values of α calculated for a non-linear fit of tracking data for EVs in the matrices (Eq. 9). Error bars represent the 95% confidence interval. SR, stress relaxing; E, elastic.
Figure 8:
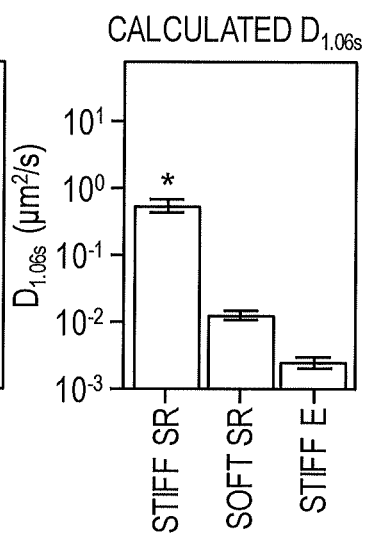
FIG. 8 shows mean $D_{1.06s}$ calculated for the tracks in FIG. 7. *P=6.9×10$^{-7}$ via a one-way ANOVA with Tukey's test for multiple comparisons. SR, stress relaxing; E, elastic.

To study whether the EV release from engineered hydrogels corresponds to individual EV transport, a three-dimensional (3D) particle-tracking approach was developed that used high-speed 3D microscopy with deconvolution to visualize and calculate the MSD of the CD63-K2S-EVs over time in different environments. Particles were tracked immediately after hydrogel formation to capture the initial behaviors possibly affected by hydrogel swelling. Data were collected every $\Delta t=0.267$ seconds over a total time $T\approx 8$ seconds. Next, data were ensemble-averaged over numerous tracks and fit to the power law form (Eq. 9; Metzler, et al. (2014) *Phys. Chem. Chem. Phys.* 16:24128-24164) to calculate an effective ensemble exponent $\alpha$ and coefficient $K_\alpha$. The effective diffusion coefficient (Eq. 12) was calculated for each track over each interval $\tau=4\Delta t\approx 1.06$ s to give Eq. 10. Multiple values for $D_{1.06s}(\tau)$ were obtained for a single track for each interval r and averaged to obtain a single $D_{1.06s}$ for each track. The method was validated by measuring the transport of NPs in glycerol solutions with different solution viscosities and thus different expected transport speeds. NPs in these solutions showed an $\alpha$ of −1, which indicated diffusive transport. Furthermore, they exhibited diffusion coefficients $D_{1.06s}$ like those expected from conventional Stokes-Einstein theory. In contrast, NPs in a stiff stress relaxing matrix exhibited a subdiffusive ($\alpha\approx 0.39$), slower (D1.06s≈0.01 µm²/s) transport, which indicated confinement. Strikingly, EVs in a stiff stress relaxing matrix showed a approaching that of NPs transporting in solution ($\alpha\approx 0.88$) (FIG. 7). EVs in a soft stress relaxing matrix exhibited a significantly lower $D_{1.06s}$ (FIG. 8) with subdiffusive transport ($\alpha\approx 0.49$), whereas EVs in a stiff elastic matrix showed a more pronounced subdiffusive transport ($\alpha\approx 0.045$), which indicated that the matrix stress relaxation allowed EVs to overcome confinement.

Figure 9:
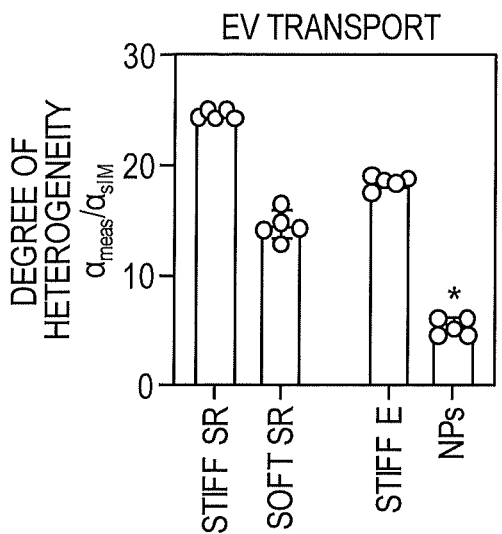
FIG. 9 shows EV transport in the matrix displays a dynamic heterogeneity, indicated by a higher standard deviation (s.d.) of $D_{1.06s}$ for the measured tracks versus the simulated tracks, $\sigma_{meas}/\sigma_{sim}$. N=5 simulations. Nanoparticles (NPs) in 80% glycerol were analyzed for N=32 tracks. Error bars denote s.e.m. *P<10$^{-15}$ via one-way ANOVA with Tukey's test for multiple comparisons. SR, stress relaxing; E, elastic.

Stress relaxing matrix systems can give rise to 'dynamic heterogeneity' (Schirmache, et al. (2015) *Phys. Rev. Lett.* 115:015901), wherein particles can escape confinement or 'cages' formed by the matrix. To determine an expected standard deviation (s.d.) of $D_{1.06s}$ for particles in a homogeneous system, tracks were simulated matched to measurement conditions. Simulated tracks followed the measured tracks for NPs transporting in solutions. The s.d. of experimentally determined $D_{1.06s}$ ($\sigma_{meas}$) was calculated and normalized to the s.d. of $D_{1.06s}$ for simulated trajectories ($\sigma_{sim}$) to measure the degree of heterogeneity of $D_{1.06s}$ (Lieleg, et al. (2010) *Biophys. J.* 98:1782-1789). Although NPs in solution followed their simulated trajectories with a lower degree of heterogeneity, $\sigma_{meas}/\sigma_{sim}$, EVs in the matrix showed a higher $\sigma_{meas}/\sigma_{sim}$ (FIG. 9), which indicated a more heterogeneous distribution of $D_{1.06s}$. To investigate this behavior, it was determined how individual EVs exhibited changes in transport motions over time by defining another 3D diffusion coefficient ($D_{0.053s}$) with shorter intervals r=2$\Delta t$0.53s to capture the local transport behaviors. $D_{0.53s}$ was calculated for each interval $\tau_i$ within the tracks to express each track as $D_{0.53s}(\tau)$. Next, the difference of $D_{0.53s}$ ($\tau$) between consecutive intervals $\tau_i$ and $\tau_{i+1}$ ($\tau_1\approx 0.53$s, $\tau_2\approx 1.06$s, ...) was taken to calculate $\Delta D_{0.53s}$:

$$\Delta D_{0.53s}(\tau_i) = D_{0.53s}(\tau_{i+1}) - D_{0.53s}(\tau_i) \quad (15)$$

which indicates the magnitude of changes in the diffusion coefficient over time within a track. To compare the spread of $\Delta D_{0.53s}$ between groups, values for $\Delta D_{0.53s}$ were normalized to the mean $\Delta D_{0.53s}$ for each group (normalized $\Delta D_{0.53s}$). From a theoretical perspective, particle motion is facilitated when $\Delta D_\tau>0$, particle motion is hindered when $\Delta D_\tau<0$ and particle motion remains constant when $\Delta D_\tau\approx 0$. $\Delta D_{0.53s}$ values were close to zero for NPs transporting in solution, which indicated that $\Delta D_{0.53s}\approx 0$ for particles that underwent free diffusion. However, individual tracks of EVs in a stiff matrix showed a much broader distribution of $\Delta D_{0.53s}$, which indicated that a stiff matrix drives the fluctuating transport motions within the tracks. Furthermore, $\Delta D_{0.53s}$ values were ~50% both positive and negative, which indicated that this behavior was associated with zero-mean fluctuations in transport motion.

Figure 10:
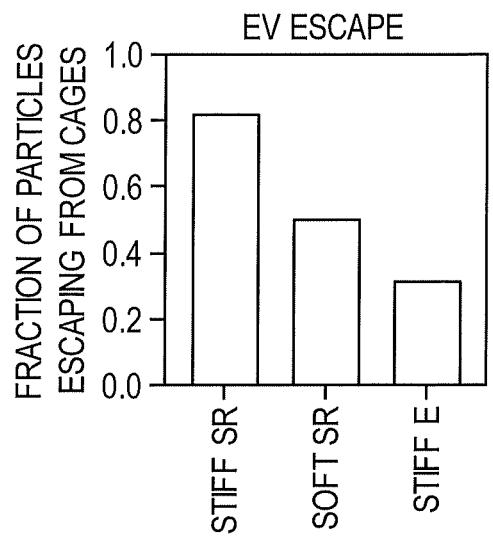
FIG. 10 shows the fraction of EVs able to escape cages of confinement for EV tracks in FIG. 7. SR, stress relaxing; E, elastic.

To calculate the extent to which EVs escaped confinement, the matrix was modelled as a system of 'cages' with a defined size c that transporting particles must overcome (Goiko, et al. (2016) *Sci. Rep.* 6:34987; Weigel, et al. (2011) *Proc. Natl Acad. Sci. USA* 108:6438-6443; Manzo, et al. (2015) *Phys. Rev.* X5:011021). As NPs in a stiff stress relaxing matrix were confined with $\alpha\approx 0.39$, c was defined as the plateau MSD for this condition (c≈0.09 µm²). Tracks were analyzed to determine whether their MSD exceeded c (the fraction of particles that escapes from the cages) and, if so, the elapsed time before the MSD exceeded c (the escape time). A significant amount of the EVs in a stiff stress relaxing matrix demonstrated the ability to escape cages and they did this more rapidly (~1.3 s) than the EVs in a soft stress relaxing matrix (FIG. 10). In contrast, EVs in a stiff elastic matrix less readily escaped cages, which further showed that matrix stress relaxation is crucial to allow EV transport. Furthermore, the radius of gyration $R_g$ (Parry, et al. (2014) *Cell* 156:183-194), defined as the time-averaged root mean square displacement over the particle trajectory, was calculated for each particle. EVs in a stiff stress relaxing matrix explored more space than EVs in a soft stress relaxing matrix, as indicated as by approximately a 10-fold higher $R_g$.

As the EVs showed the ability to transport in confined spaces, it was posited that intrinsic EV properties also drive their transport. Although lyophilized (freeze-dried) EVs possessed the same size distribution as freshly isolated EVs, they did not exhibit a greater release from the stiff stress relaxing hydrogel, a feature that was further confirmed by a decrease in $D_{1.06s}$ by about ten-fold and in α to ~0.25. Non-lyophilized EVs with an integral membrane structure are likely required for mechanically sensitive transport, as lyophilizing EVs can compromise their membrane integrity (Kusuma, et al. (2018) *Front. Pharmacol.* 9:01199). This is supported by the addition of the cryoprotectant trehalose to EV preparations during lyophilization (Frank, et al. (2018) *Sci. Rep.* 8:12377), which recovered release behavior. It was contemplated that transport may be regulated by EV surface interactions within hydrogels or actomyosin contractility within EVs. However, tethering the integrin binding ligand RGD (~0.8 μM) within hydrogels or treating hydrogels with myosin-II (blebbistatin) and Rho-associated protein kinase (Y27632) inhibitors did not affect the EV release. Importantly, ATP within EV preparations existed at a concentration much less than that in cells, and EVs from cells partially (~50%) depleted of ATP did not release differently, which indicated that EV transport mechanisms were likely metabolically passive rather than active.

The results describe the ability of EVs to transport in a polymer matrix with an absence of matrix degradation, despite EVs being larger than the average mesh size of the matrices. The matrix stress relaxation allowed the EVs to readily escape cages formed by the polymer network. A stiff matrix increased the fluctuating EV transport motions, and thus the combination of stiffness and stress relaxation led to a greatly enhanced EV transport.

EXAMPLE 3

Modulation of AQP1

Water permeation via aquaporins drives the migration of spatially confined cells independent of myosin-II (Stroka, et al. (2014) *Cell* 157:611-623). As aquaporins are partitioned into EVs (Blanc, et al. (2009) *Blood* 114:3928-3934), it was posited that water permeation through aquaporins regulates EV transport. In this respect, EV release in both stiff and soft stress relaxing hydrogels was increased by the addition of 3% polyethylene glycol but did not occur if the EVs were freeze-dried. In addition, the ion channel inhibitor, tetrodotoxin (a sodium channel inhibitor), significantly increased EV release in soft and stiff stress relaxing hydrogels, whereas NPPB (a chloride channel inhibitor) and EIPA (a Na(+)/H(+) exchanger) did not alter EV release from the hydrogels. Similarly, GsMTx4 (a selective inhibition of cation-permeable mechanosensitive channels), increased EV release in stiff stress relaxing hydrogels.

Figure 11:
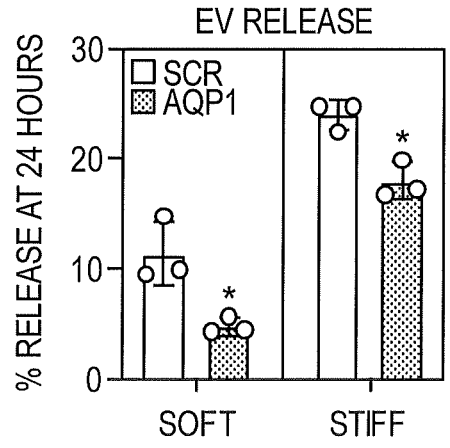
FIG. 11 shows that EVs depleted of aquaporin 1 with an AQP1 siRNA (AQP1) exhibited a significantly lower mean % released from stress relaxing hydrogels. N=3 hydrogels for each condition. *P=0.021 (soft), P=8.6×10$^{-3}$ (stiff) via an unpaired two-tailed t-test. Scrambled siRNA, Scr.

It was then determined whether aquaporins were required for EV release. AQP1 is the dominant aquaporin isoform expressed in MSCs. Treating cells with short interfering RNA (siRNA) against AQP1 lead to an ~80% mRNA knockdown in cells and a ~60% reduction in the AQP1 protein packaged into EVs. AQP1 depletion in EVs significantly increased their Young's modulus (~70 MPa for scrambled siRNA vs. ~200 MPa for AQP1 siRNA), which indicated that water permeation made the EVs more deformable. AQP1 depletion in EVs significantly decreased the EV release from hydrogels (FIG. 11), and AQP1-depleted EVs showed an impaired release from decellularized matrices, which indicated that the greater deformability via AQP1 enhanced the EVs ability to transport in the matrix. Although AQP1 depletion reduced $D_{1.06s}$ by about three-fold, α remained unchanged for individual EVs. Liposomes encapsulated in the stiff stress relaxing matrix exhibited α≈0.65 with a much lower $D_{1.06s}$, which indicated that the presence of lipid membrane alone is not sufficient for an enhanced EV transport. Pulling values from all the experimental groups of EVs in a matrix showed that α increased with increased $D_{1.06s}$, but became saturated near α≈1.0 when $D_{1.06s}$ was higher than 0.1 μm²/s, which indicated that a three-fold decrease in $D_{1.06s}$ via AQP1 depletion was less likely to be sufficient to significantly decrease α. Consistent with these results, AQP1-depleted EVs exhibited a significantly slower mean escape time than that of the control EVs in a stiff stress relaxing matrix (approximately two-fold slower, P=2.1× $10^{-7}$ via an unpaired two-tailed t-test). Finally, AQP1 depletion did not affect the spread of $\Delta D_{0.53s}$, which indicated the independence of AQP1 with fluctuating transport motion.

Figure 12:
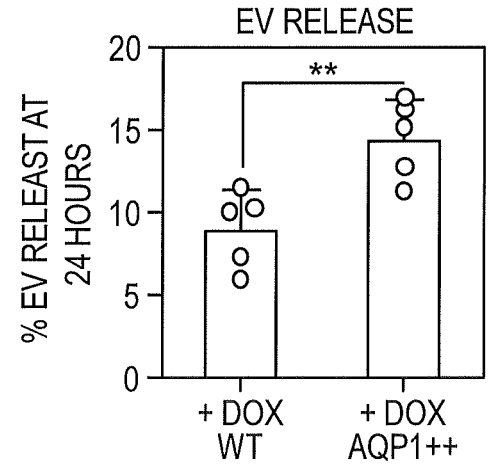
FIG. 12 shows that doxycycline (Dox) inducible overexpression of AQP1 enhances EV release from a soft stress relaxing hydrogel. Mesenchymal stem cells (MSCs) were genetically engineered to upregulate AQP1 protein only in the presence of doxycycline. After doxycycline treatment of MSCs for 2 days, EVs with increased AQP1 (AQP1++) were collected and encapsulated in a soft stress relaxing, ionically crosslinked alginate hydrogel, followed by measurement of EV release in 24 hours. **p<0.01, n=5 gels.

To demonstrate the positive effect AQP1 has on EV release, MSCs were transduced with a construct where AQP1 expression is under control of a tetracycline-dependent promoter system. AQP1 expression was induced for 2 days with doxycycline After doxycycline treatment of MSCs, EVs with increased AQP1 (AQP1++) were collected and encapsulated in a soft stress relaxing, ionically cross-linked alginate hydrogel as described herein. EV release from the hydrogel was then assessed after 24 hours. This analysis (FIG. 12) indicated that overexpression of AQP1 enhanced EV release from a soft stress relaxing hydrogel.

The results indicated that EVs subjected to water permeation through AQP1 allowed the EVs to become more deformable by altering their volume, which enabled their escape from confinement. The observation that AQP1 mediates EV deformability and the resulting transport in ECM is important because the deformability of synthetic nanoparticles with lipid bilayers was recently shown to dramatically affect their accumulation in tissues both in vitro and in vivo (Guo, et al. (2018) *Nat. Commun.* 9:130). As such, the results presented herein provide insight as to how therapeutic EVs, as well as other delivery vesicles (e.g., liposomes, nanoparticles, platelets, red blood cells, or therapeutic cells) can be modified to modulate their delivery through tissue ECM.

EXAMPLE 4

Tuning Stress Relaxation Time of Hydrogels

Figure 13:
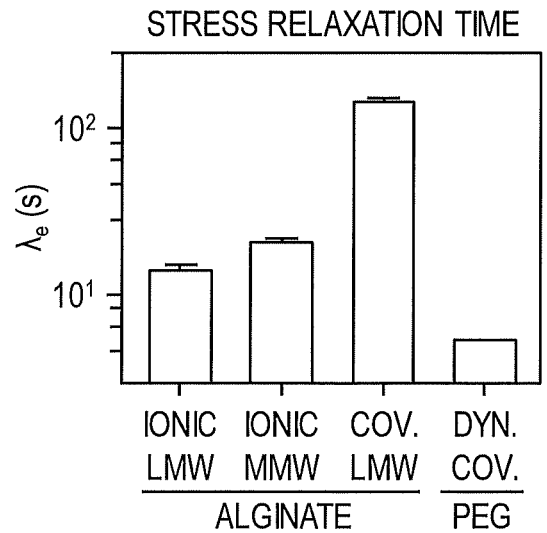
FIG. 13 shows the stress relaxation time of different hydrogel formulations ($\lambda_e$). LMW, Low molecular weight; MMW, Medium molecular weight; Cov., covalent crosslinking; Dyn. Cov., dynamic covalent crosslinking.

EVs were encapsulated in a PEG hydrogel or alginate hydrogels composed of low molecular weight alginate or high molecular weight alginate and either ionic or covalent crosslinking. The stress relaxation times of the different hydrogel formulations ($\lambda_e$) was determined (FIG. 13). In addition, transport of EVs in the hydrogels with the different stress relaxation times was measured by nanoscale live imaging. This analysis indicated that the EVs in the ionically cross-linked LMW and MMW alginate demonstrated the ability to escape the hydrogels more rapidly (λ~15 s and λ~21 s, respectively) than the covalently crosslinked LMW alginate hydrogel (λ~148 s); However, the dynamic covalently crosslinked PEG hydrogel allowed for more rapidly (λ~5.4 s) escape of the EVs.

EXAMPLE 5

Therapeutic Effect of EVs

To confirm that EVs derived from MSCs showed a therapeutic effect, a lipopolysaccharide (LPS)-induced model of acute lung injury (ALI) in mice was used. Mice were treated with 10 mg/kg LPS to induce injury followed by treatment with EVs 4 hours later. After 24 hours, mice are evaluated for vascular permeability and pulmonary edema. Mice receiving MSC-EVs showed a significantly lower permeability and edema, demonstrating that EVs exhibited a therapeutic effect against ALI. To further demonstrate the role of AQP1, mice (n=2) were treated with LPS i.p. (10 mg/kg), followed by i.v. injection of EVs from MSCs treated with scrambled or AQP1 siRNA. Wet/dry ratio of lung tissue was assessed 24 hours after EV injection. In addition, Evans Blue Albumin extravasation in lung vs. blood was carried out as a measure of vascular permeability. This analysis indicated that AQP1 is essential for EVs to resolve lipopolysaccharide-mediated lung injury.

What is claimed is:

1. A recombinant extracellular vesicle (EV) comprising a genetically modified number of one or more water channel proteins on the surface of the EV compared to a naturally-occurring EV, the genetically modified number of one or more water channel proteins on the surface of the EV being a result of isolating the EV from a recombinant producer cell genetically modified to express an increased level or decreased level of the one or more water channel proteins as compared to a naturally-occurring producer cell.

2. The recombinant EV of claim 1, said recombinant EV isolated from a recombinant producer cell harboring a nucleic acid construct encoding the one or more water channel proteins.

3. A composition comprising extracellular vesicles (EVs) encapsulated in a matrix, wherein the EVs comprise a genetically modified number of one or more water channel proteins on the surface of the EVs compared to a naturally-occurring EVs, the genetically modified number of one or more water channel proteins on the surface of the EVs being a result of isolating the EVs from a recombinant producer cell genetically modified to express an increased level or decreased level of the one or more water channel proteins as compared to a naturally-occurring producer cell.

4. The composition of claim 3, wherein the EVs are isolated from a recombinant producer cell harboring a nucleic acid construct encoding the one or more water channel proteins.

5. The composition of claim 3, wherein the matrix is a hydrogel or artificial extracellular matrix.

6. The composition of claim 5, wherein the hydrogel has a complex modulus G* in the range of 0.3 kPa to 3 kPa.

7. The composition of claim 5, wherein the hydrogel exhibits a stress relaxation rate between 10 seconds and 100 seconds.

8. A method of controlling release of extracellular vesicles (EVs) from an encapsulating matrix comprising genetically modifying the number of one or more water channel proteins on the surface of said EVs thereby controlling the release of the EVs from the encapsulating matrix,
wherein the genetically modified number of one or more water channel proteins on the surface of the EVs is a result of isolating the EV from a recombinant producer cell genetically modified to express an increased level or decreased level of the one or more water channel proteins as compared to a naturally-occurring producer cell.

9. The method of claim 8, wherein the number of one or more water channel proteins on the surface of said EVs is increased or decreased by isolating EVs from a recombinant producer cell harboring a nucleic acid construct encoding the one or more water channel proteins.

10. The method of claim 8, wherein the activity of the one or more water channel proteins on the surface of said EVs is by exposing the EVs to a hypertonic medium or one or more ion channel inhibitors.

11. The method of claim 8, wherein the number of one or more water channel proteins on the surface of said EVs is increased or decreased by isolating EVs from a recombinant producer cell harboring a nucleic acid construct encoding one or more siRNAs that inhibit the expression of the one or more water channel proteins.

12. A method for treating a subject comprising administering to a subject in need of treatment with extracellular vesicles (EVs) an effective amount of the composition of claim 3 thereby treating the subject.

13. The method of claim 12, wherein the subject is suffering from a lung injury.

14. The method of claim 13, wherein the lung injury comprises endotoxin-induced acute lung injury, infection-mediated lung injury, or fibrotic lung injury.

* * * * *

SEQUENCE LISTING

<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Gly Gly Gly Gly Arg Gly Asp Ser Pro
1               5

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
acatcgctca gacaccatg                                                   19

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
tgtagttgag gtcaatgaag gg                                               22

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ctggcgattg actacactgg                                                  20

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
aagtcataga tgagcactgc c                                                21

<210> SEQ ID NO 6
<211> LENGTH: 21
<212> TYPE: DNA
<213> ORGANISM: Artificial Sequence

```
<220> FEATURE:
<223> OTHER INFORMATION: Synthetic oligonucleotide

<400> SEQUENCE: 6
ttggtttctc tgttaccctg g                                            21

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 7
aacgggctgg attcatgg                                                18

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ctttgccacc tatccctctg                                              20

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
ccacagtgaa agcctccag                                               19

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
gcttagatct ggcttccaaa gg                                           22

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
aatgtccaca cttaccccac                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ctccccagcc ttatccattg                                              20
```

```
<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
acccagaaga cccagtgag                                                19
```